United States Patent
Kim et al.

(10) Patent No.: US 10,648,024 B2
(45) Date of Patent: May 12, 2020

(54) POROUS STRUCTURE AND METHOD FOR MANUFACTURING SAME

(71) Applicant: Korea Institute of Science and Technology, Seoul (KR)

(72) Inventors: Sang Kyung Kim, Seoul (KR); Nakwon Choi, Seoul (KR); Dong Jin Lee, Seoul (KR); Seungwon Jung, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 95 days.

(21) Appl. No.: 15/032,541

(22) PCT Filed: Oct. 28, 2014

(86) PCT No.: PCT/KR2014/010171
§ 371 (c)(1),
(2) Date: Apr. 27, 2016

(87) PCT Pub. No.: WO2015/065005
PCT Pub. Date: May 7, 2015

(65) Prior Publication Data
US 2016/0265028 A1 Sep. 15, 2016

(30) Foreign Application Priority Data
Oct. 28, 2013 (KR) .................. 10-2013-0128696

(51) Int. Cl.
*B01L 3/00* (2006.01)
*C12Q 1/686* (2018.01)

(52) U.S. Cl.
CPC .......... *C12Q 1/686* (2013.01); *B01L 3/50851* (2013.01); *B01J 2219/00317* (2013.01);
(Continued)

(58) Field of Classification Search
CPC ............ C12Q 1/6861; C12Q 2537/143; C12Q 2563/159; C12Q 2565/519; C12Q 1/686;
(Continued)

(56) References Cited

U.S. PATENT DOCUMENTS 7,955,802 B2 6/2011 Whitman et al.
2004/0241713 A1 12/2004 Mirzabekov et al.
(Continued)

FOREIGN PATENT DOCUMENTS

CN 1861800 A 11/2006
CN 101395279 A 3/2009
(Continued)

OTHER PUBLICATIONS

Strizhkov et al., PCR Amplification on a Microarray of Gel-Immobilized Oligonucleotides: Detection of Bacterial Toxin- and Drug-Resistant Genes and Their MutationsBiotechniques, vol. 29, pp. 844-857 (Year: 2000).*
(Continued)

*Primary Examiner* — Teresa E Strzelecka
(74) *Attorney, Agent, or Firm* — NSIP Law

(57) ABSTRACT

A porous structure according to the present invention has a polymerase chain reaction (PCT) primer inside pores thereof, and hence, even an inner portion thereof can be used unlike general structures of which only surfaces are used for amplification and detection, thereby maximizing reactivity. In addition, the differentiating of the kinds of primers contained in respective structures leads to detection of several kinds of target nucleic acids at the same and real-time analysis thereof at the same time, and thus is useful for multiplex real-time PCR.

13 Claims, 10 Drawing Sheets

Specification includes a Sequence Listing.

(52) U.S. Cl.
CPC ............... *B01J 2219/00644* (2013.01); *B01J 2219/00648* (2013.01); *B01J 2219/00722* (2013.01); *B01L 2200/16* (2013.01); *B01L 2300/069* (2013.01); *B01L 2300/0819* (2013.01)

(58) Field of Classification Search
CPC .... B01J 2219/00317; B01J 2219/00644; B01J 2219/00648; B01J 2219/00722; B01L 2200/16; B01L 2300/069; B01L 2300/0819; B01L 3/50851; B01L 3/5085
See application file for complete search history.

(56) References Cited

U.S. PATENT DOCUMENTS

| | | |
|---|---|---|
| 2006/0263799 A1 | 11/2006 | Dertinger et al. |
| 2009/0203083 A1 | 8/2009 | Mauritz |
| 2013/0005591 A1 | 1/2013 | Cai |
| 2014/0335531 A1 | 11/2014 | Tamaoki et al. |

FOREIGN PATENT DOCUMENTS

| | | |
|---|---|---|
| CN | 102757517 A | 10/2012 |
| KR | 10-0794699 B1 | 1/2008 |
| KR | 10-2008-0103548 A | 11/2008 |
| KR | 10-2016-0033393 A | 3/2016 |
| WO | WO 2007/098914 A1 | 7/2007 |
| WO | WO 2009/039202 A1 | 3/2009 |
| WO | WO 2011/068518 A1 | 6/2011 |

OTHER PUBLICATIONS

Tamagawa et al., Pores and diffusion characteristics of porous gels, Polymer, vol. 41, pp. 7201-7207, (Year: 2000).*
Atrazhev et al., In-Gel Technology for PCR Genotyping and Pathogen DetectionAnal. Chem., vol. 82, pp. 8079-8087 (Year: 2010).*
Guo et al., Direct fluorescence analysis of genetic polymorphisms by hybridization with oligonucleotide arrays on glass supports, Nucl. Acids Res., vol. 22, pp. 5456-5465 (Year: 1994).*
Chavda, H.V. et al., Effect of crosslinker concentration on characteristics of superporous hydrogel, Int. J. Pharmaceut. Invest., vol. 1, pp. 17-21 (Year: 2011).*
Meiring, J.E. et al., Hydrogel Biosensor Array Platform Indexed by Shape, Chem. Mater., vol. 16, pp. 5574-5580 (Year: 2004).*
Buwalda, S.J. et al., Hydrogels in a historical perspective: From simple networks to smart materials, J. Control. Release, vol. 190, pp. 254-273 (Year: 2014).*
Yershov, G. et al., DNA analysis and diagnostics on oligonucleotide microchips, PNAS, vol. 93, pp. 4913-4918 (Year: 1996).*
Strizhkov, Boris N., et al., "PCR amplification on a microarray of gel-immobilized oligonucleotides: detection of bacterial toxin-and drug-resistant genes and their mutations." Biotechniques 29.4, 2000 (1 page).
Wu, Ying, et al. "Quantitative assessment of a novel flow-through porous microarray for the rapid analysis of gene expression profiles." Nucleic Acids Research 32.15, 2004 (1 page).
Huang, Huan, et al. "A gel-based solid-phase amplification and its application for SNP typing and sequencing on-chip." Analyst 134. 12, 2009 (2434-2440).
International Search Report dated Feb. 5, 2015 in counterpart International Application No. PCT/KR2014/010171 (6 pages, in Korean, with English language translation).
Written Opinion of the International Searching Authority dated Feb. 5, 2015 in counterpart International Application No. PCT/KR2014/010171 (5 pages, in Korean).
Chinese Office Action dated Jun. 2, 2017 in corresponding Chinese Patent Application No. CN 201480065116.1 (6 pages in Chinese).
Choi, Nak Won, et al. "Multiplexed detection of mRNA using porosity-tuned hydrogel microparticles." Analytical chemistry 84.21 (2012) (9 pages in English).
European Search Report dated May 26, 2017 in corresponding European Patent Application No. 14857332.2 (19 pages in English).
Jung, Seungwon, et al. "Extensible multiplex real-time PCR for rapid bacterial identification with carbon nanotube composite microparticles." Biosensors and Bioelectronics 94 (2017): 256-262.
Jung, Seungwon, et al. "Extensive Multiplex Real-time PCR of MicroRNA Using Microparticles." Scientific reports 6 (2016).
Jung, Seungwon, et al. "Particle-based Highly Multiplexable Real-time PCR for MicroRNA Profiling." Center for BioMicrosystems, Korea Institute of Science and Technology, Korea, (2015) (3 Pages in English).
Kim, Hwan-Gon, et al. "Preparation of Monodisperse ENX-Loaded PLGA Microspheres Using a Microfluidic Flow-Focusing Device." Journal of Biobased Materials and Bioenergy 7.1 (2013): (7 pages in English).
Seungwon Jung et al., 19th International Conference on Miniaturized Systems for Chemistry and Life Sciences, 2015, (3 pages in English).
Chinese Office Action dated Feb. 24, 2018 in corresponding Chinese Patent Application No. 201480065116.1 (2 pages in English; 9 pages in Chinese).

* cited by examiner

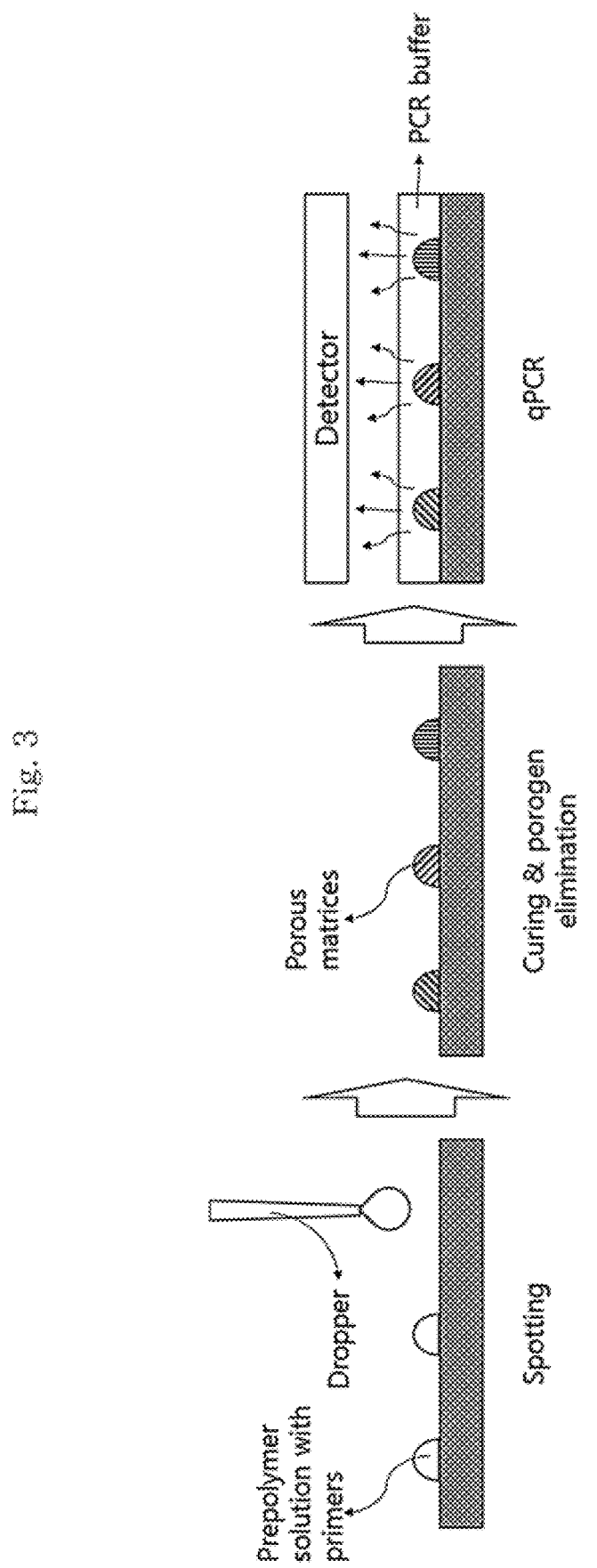

Fig. 8
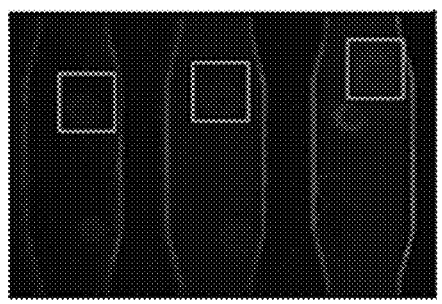
Before qPCR
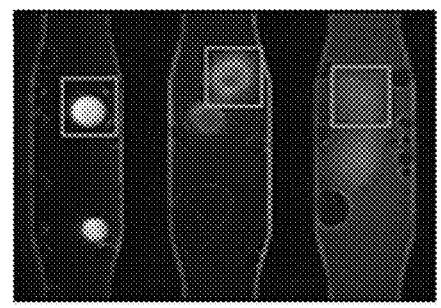
After qPCR

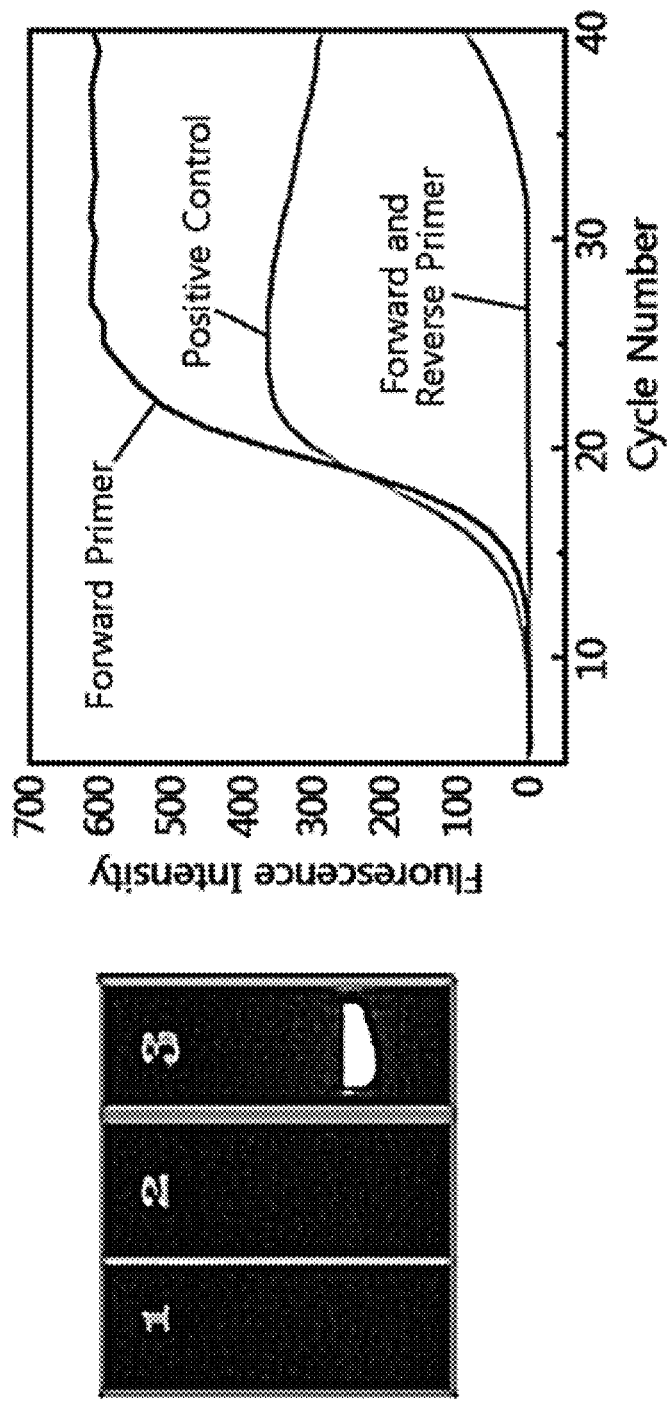

- Ch1 : Hydrogel solution (short forward and short reverse primer) + UV curing + Rinsing with TE (5 Times)
- Ch2 : Hydrogel solution (long forward and long reverse primer) + UV curing + Rinsing with TE (5 Times)
- Ch3 : Positive control

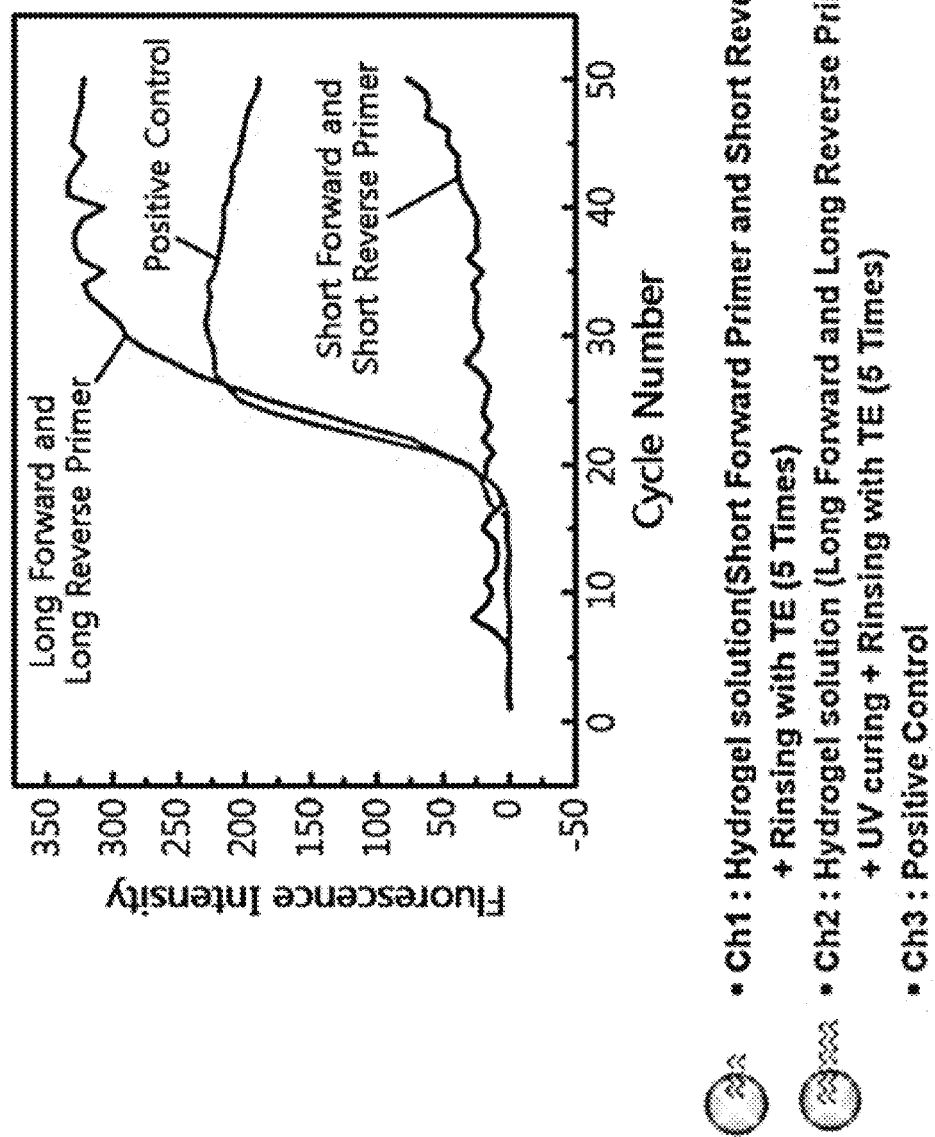

SEQUENCE LISTING

```
<160> NUMBER OF SEQ ID NOS: 2

<210> SEQ ID NO 1
<211> LENGTH: 29
<212> TYPE: DNA
<213> ORGANISM: Artificial Sequence
<220> FEATURE:
<223> OTHER INFORMATION: Forward primer

<400> SEQUENCE: 1
aattatcgcc acgttcgggc aattcgtta                                          29

<210> SEQ ID NO 2
<211> LENGTH: 29
<212> TYPE: DNA
<213> ORGANISM: Artificial Sequence
<220> FEATURE:
<223> OTHER INFORMATION: Reverse primer

<400> SEQUENCE: 2
tcaataatac cggccttcaa atcggcatc                                          29
```

POROUS STRUCTURE AND METHOD FOR MANUFACTURING SAME

CROSS-REFERENCE TO RELATED PATENT APPLICATIONS

This Application is a U.S. National Phase Application under 35 U.S.C. § 371 of International Application No. PCT/KR2014/010171, filed Oct. 28, 2014, published as WO 2015/065005 on May 7, 2015, which claims the benefit of Korean Patent Application No. 10-2013-0128696, filed on Oct. 28, 2013, in the Korean Intellectual Property Office, the entire disclosures of which are incorporated herein by reference for all purposes.

TECHNICAL FIELD

The disclosure described in this specification relates to a porous structure including a primer, a manufacturing method of the porous structure, and a multiplex real-time nucleic acid amplifying method using the porous structure.

BACKGROUND ART

The polymerase chain reaction (PCR) method is a technique to amplify a nucleic acid by cloning the base sequence thereof, and there are an endpoint PCR and a real-time PCR. Hitherto, the endpoint PCR has been often used, but by this method, it is possible to detect or quantify the amplified nucleic acid only after the PCR reaction is completed, and thus there is a problem that a separate result analysis step such as electrophoresis and an apparatus for that are required after the experiment, a long time of 2 hours or longer is required, and it is not possible to detect or quantify the amplified nucleic acid in real time. For example, the first nucleic acid is required to be quantified from the PCR product obtained after the reaction is completed, but it is difficult to accurately quantify the first nucleic acid due to various factors which affect the analysis even if fluorescent staining or the like is employed. The accurate amount of a nucleic acid is measured at the exponential phase, but it is difficult to analyze the accurate amount by the endpoint PCR since a real-time measurement is impossible by it.

In contrast, the real-time PCR has an advantage that the first target nucleic acid can be accurately quantified since the amount of the amplified nucleic acid is measured for every cycle and particularly the reaction in the exponential phase that is the section in which the amplification takes place can be confirmed in real time through a monitor. In particular, the multiplex real-time nucleic acid amplifying method (multiplex real-time PCR) is widely used in the disease diagnostic field since it is possible to confirm various biomarkers in a single chamber by one time of experiment and to quantitatively analyze them in real time.

However, it is difficult to conduct an accurate measurement by a method that is the most commonly used method for multiplex real-time nucleic acid amplification and uses the color of the probe and the melting point of the primer since the interference between the targets increases as the number thereof to be measured increases. Hence, it is difficult to use the multiplex real-time nucleic acid amplifying method in the fields that require an accurate diagnosis of diseases through simultaneous and rapid analysis of many different kinds of nucleic acids such as point-of-care technology (POCT).

CITATION LIST

Patent Literature

[Patent Literature 1]
  Korea Patent Registration No. 10-0794699
[Patent Literature 2]
  Korea Patent Application Laid-Open No. 10-2008-0103548

SUMMARY OF INVENTION

Technical Problem

An object of the present invention is to provide a porous structure that is a structure for multiplex real-time nucleic acid amplification (multiplex real-time PCR), a manufacturing method of the porous structure, and a multiplex real-time nucleic acid amplifying method that can simultaneously and accurately analyze various kinds of nucleic acids in real time by using the structure.

Solution to Problem

In order to achieve the above object, an embodiment of the present invention provides a porous structure including pores,
the porous structure including primers in one or more directions between a forward primer and a reverse primer of a target nucleic acid as a primer of polymerase chain reaction (PCR) fixed to the interior of the pores.

In addition, an embodiment of the present invention provides a method for manufacturing a porous structure, the method including:
  preparing a structure-forming solution containing a prepolymer, a porogen, and primers in one or more directions between a forward primer and a reverse primer of a target nucleic acid as a primer of polymerase chain reaction (PCR);
  forming a structure in a droplet form by allowing oil to pass through one channel of micro-channels consisting of two channels including a section to cross each other at right angles and allowing the structure-forming solution prepared above to pass through the other channel so as to disperse the structure-forming solution in an oil phase in the crossing section;
  curing the structure thus formed; and
  forming pores in the structure by removing the porogen from the cured structure.

Another embodiment of the present invention provides a method for manufacturing a porous structure, the method including:
  preparing a structure-forming solution containing a prepolymer, a porogen, and primers in one or more directions between a forward primer and a reverse primer of a target nucleic acid as a primer of polymerase chain reaction (PCR);
  forming a structure in a droplet form by spotting the structure-forming solution prepared above on an array;
  curing the structure; and
  forming pores in the structure by removing the porogen from the cured structure.

Still another embodiment of the present invention provides an apparatus for multiplex real-time nucleic acid amplification including:
  one or more porous structures described above; and
  an array having a surface patterned in a well form so that the porous structure is arranged.

In addition, an embodiment of the present invention provides a multiplex real-time nucleic acid amplifying method including:

injecting one or more porous structures described above into a chamber including an array having a surface patterned in a well form and arranging the porous structures on the array;

injecting a solution containing one or more target nucleic acids into the chamber and introducing the solution into a pore of the porous structure; and amplifying the target nucleic acid through the polymerase chain reaction (PCR) of the target nucleic acid.

Advantageous Effects of Invention

The porous structure according to the present invention has a primer of polymerase chain reaction (PCR) in the interior of the pores, and thus even the interior of the structure can be utilized in the amplification and detection unlike a typical structure of which only the surface is used so that the reactivity is maximized.

In addition, the porous structure is used in multiplex real-time nucleic acid amplification (multiplex real-time PCR) since it is possible to simultaneously detect various kinds of target nucleic acids and at the same time to analyze these in real time by varying the kinds of primers included in the respective structures, and the porous structure is useful for the fields that require an accurate diagnosis of diseases through simultaneous and rapid analysis of many different kinds of nucleic acids such as point-of-care technology (POCT).

BRIEF DESCRIPTION OF DRAWINGS

FIG. 3 is a schematic diagram illustrating a method for manufacturing a porous structure according to an embodiment of the present invention, specifically it illustrates a step of forming a porous structure in a droplet form by spotting a porous structure-forming solution on an array; a step of curing the porous structures that are manufactured in a droplet form and have different kinds of targets from one another and removing the porogen from the porous structures; and a step of amplifying a nucleic acid and at the same time detecting it in real time.

FIG. 8 is a diagram illustrating photographs of the porous structure according to an embodiment of the present invention taken before and after the quantitative PCR using a CCD camera.

FIG. 9 illustrates a photograph (left) of the porous structure Ch1-3 according to an embodiment of the present invention subjected to electrophoresis in order of from channel 1 to channel 3 and then measurement and a graph of fluorescence intensity measured for every cycle.

FIG. 11 illustrates a graph of the fluorescence intensity of the porous structure Ch1-3 according to an embodiment of the present invention measured for every cycle.

DESCRIPTION OF EMBODIMENTS

Hereinafter, the present invention will be described in detail.

An embodiment of the present invention provides a porous structure including pores, and the porous structure includes primers in one or more directions between a forward primer and a reverse primer of a target nucleic acid as a primer of polymerase chain reaction (PCR) fixed to the interior of the pores.

At this time, the primers may be from 10 to 100 base pairs (bp) and more specifically from 20 to 50 base pairs, but the kind and length of the sequence of the primers can be modified depending on the target nucleic acid without limitation.

The porous structure according to an embodiment of the present invention may be one in which both the forward primer and the reverse primer of the target nucleic acid are fixed as the primer of polymerase chain reaction (PCR), or it may be one in which a primer only in one direction between these is fixed. The reactivity is enhanced as the other kind of primer can freely move in the pores in the porous structure by injecting the other kind of primer into the apparatus for multiplex real-time nucleic acid amplification (multiplex real-time PCR) utilizing the porous structure in the case of fixing a primer only in one direction between the forward primer and the reverse primer.

The porous structure according to an embodiment of the present invention, for example, may have a particle size of from 10 μm to 500 μm, and more specifically, it may have a particle size of from 100 μm to 300 μm. The shape thereof is not limited as long as it is a three-dimensional structure capable of having pores in the interior thereof, and more specifically, a spherical shape may be exemplified. As the material for the porous structure, a pre-polymer capable of being cured can be used without limitation, and specifically, a hydrophilic polymer such as polyethylene glycol-diacrylate (PEG-DA) or polyacrylamide (PA) can be used. In addition, the porosity of the porous structure as an embodiment is from 10 vol % to 80 vol % and more specifically from 50 vol % to 70 vol % with respect to the total volume of the porous structure. There is a problem that the porous property may deteriorate or the stability of the structure may deteriorate when the porosity is out of the above range.

Figure 1:
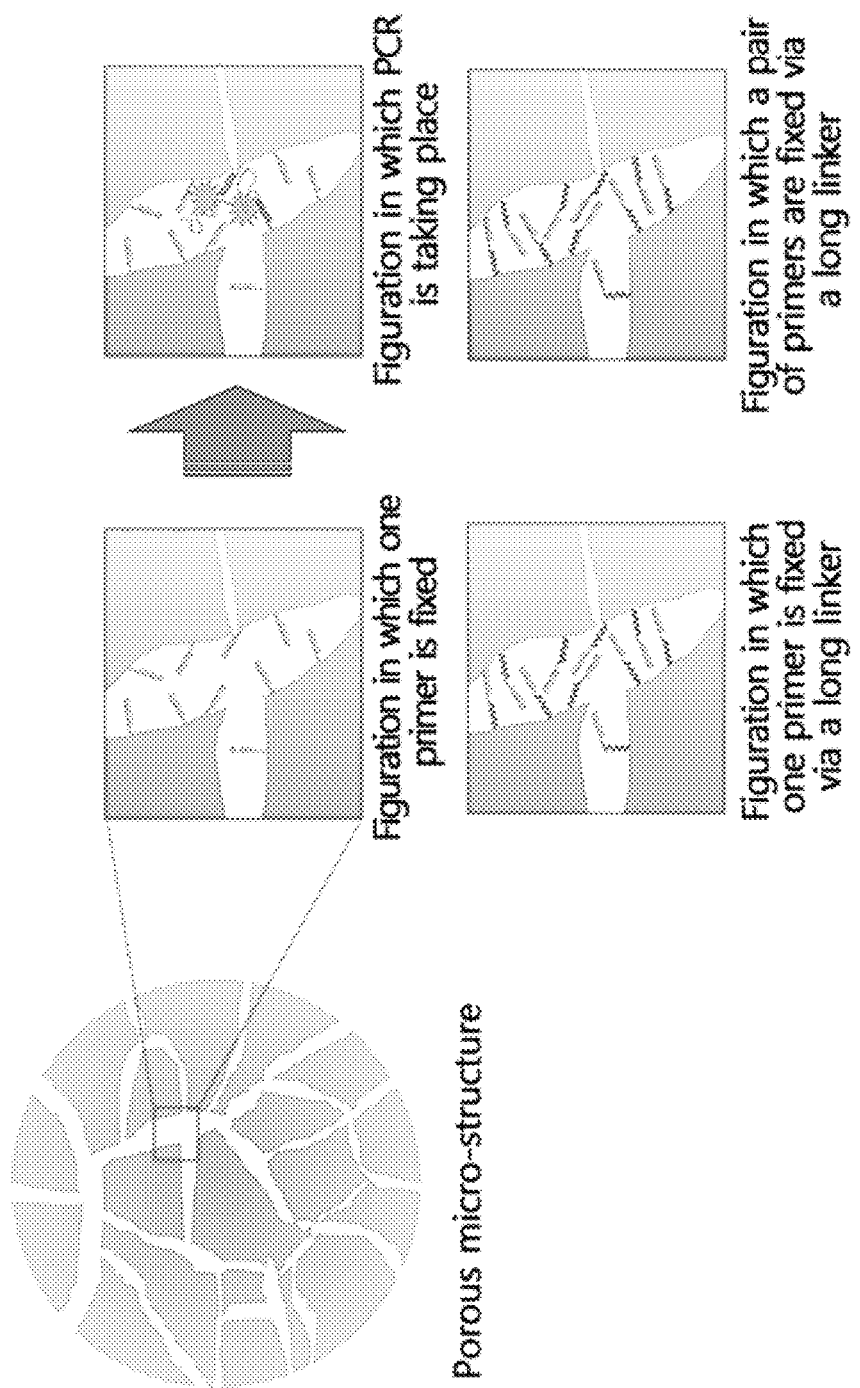
FIG. 1 illustrates the internal structure of the porous structure according to an embodiment of the present invention, and the sphere on the left is a schematic diagram of the porous structure according to an embodiment of the present invention. Specifically, the diagram on the upper-left among the four boxes on the right illustrates a figuration in which a primer in one direction between a forward primer and a reverse primer of a target nucleic acid is fixed as the primer of polymerase chain reaction (PCR), the diagram on the upper-right illustrates a figuration in which the polymerase chain reaction (PCR) of the target nucleic acid bonded with this primer is taking place, the diagram on the lower-left illustrates a figuration in which a primer in one direction between the forward primer and the reverse primer is fixed and this primer is fixed via a linker, and the diagram on the lower-right illustrates a figuration in which both the forward primer and the reverse primer are fixed via a linker.

The porous structure according to another embodiment of the present invention may be a porous structure to which a primer is fixed as the acryl group at the terminal of the primer is chemically bonded to the porous structure by including a primer having an acryl group at the terminal. In addition, as an embodiment, the primer may be linked to the porous structure via a linker, and the reactivity is enhanced as the degree of freedom of the primer that the primer is movable in the pores is increased by the linker in this case. The linker, for example, has a length of from 5 nm to 100 nm or from 20 nm to 50 nm. A polymer such as polyethylene glycol or a polymer chain such as an alkyl chain may be used as a linker, but the kind of the linker is not limited as long as it can be chemically bonded to the primer and the porous structure (see FIG. 1).

In addition, as an embodiment of the present invention, the porous structure may further include one or more between an encoder to provide the information of the fixed primer and a fluorescent marker to provide the quantitative information of the nucleic acid to be amplified in the pores. The encoder means a material that distinguishes the fixed primers fixed in the respective porous structures from one another by the color, shape, or the like, and for example, a quantum dot exhibits fluorescence in various colors or a metal, a plastic, glass, silicone, or the like which has a specific shape may be used. Alternatively, the primers in the respective porous structures may be distinguished from one another by using the porous structures having different sizes from one another or specifying the locations of the respective porous structures in the array without using the encoders.

The fluorescent marker makes it possible to detect the target nucleic acid in real time as it is bonded to the target nucleic acid to provide a fluorescent signal. The target nucleic acid to be amplified can be quantified by detecting the fluorescence intensity as the fluorescent marker can be fixed to the porous structure and the fluorescence intensity also increases in a case in which the target nucleic acid is amplified by the polymerase chain reaction. As the fluorescent marker, any one may be used without being limited by the kind as long as it exhibits fluorescence by being complementarily bonded to the target nucleic acid. For example, it is possible to use a cyanine-based dye such as SYBR® Green I, an interchelator that is bonded to a double-stranded nucleic acid to exhibit fluorescence as it is amplified such as EtBr, the TaqMan™ probe of a nucleic acid of which the 5' terminal is modified with a fluorescent substance (FAM or the like) and the 3' terminal is modified with a quencher substance (TAMRA or the like), and the like. At this time, the TaqMan™ probe is specifically bonded to a template DNA by hybridization in the annealing step but the generation of fluorescence is suppressed by the quencher on the probe, the TaqMan™ probe bonded to the template by hybridization is decomposed by the activity of 5'→3' exonuclease belonging to the Taq DNA polymerase at the time of extension reaction, the fluorescent dye is isolated from the probe, thus the suppression by the quencher is released, and fluorescence is exhibited. Alternatively, for example, it is also possible to use an oligo-nucleotide probe (Molecular Beacon probe) which forms a hairpin-shaped secondary structure and in which both terminals of the nucleic acid are modified with a fluorescent substance (FAM, TAMRA, or the like) and a quencher substance (DABCYL or the like). At this time, the molecular beacon probe forms a hairpin structure in an isolated state and the generation of fluorescence is suppressed as the fluorescent substance and the quencher substance are closely present to each other. The probe is specifically bonded to the template by hybridization in a complementary region in the annealing step, at this time, the suppression by the quencher substance is released as the distance of the fluorescent substance from the quencher substance increases, and thus the fluorescent dye on the probe exhibits fluorescence. Meanwhile, the molecular beacon probe that is not bonded by hybridization does not exhibit fluorescence as it maintains the hairpin structure.

Figure 2:
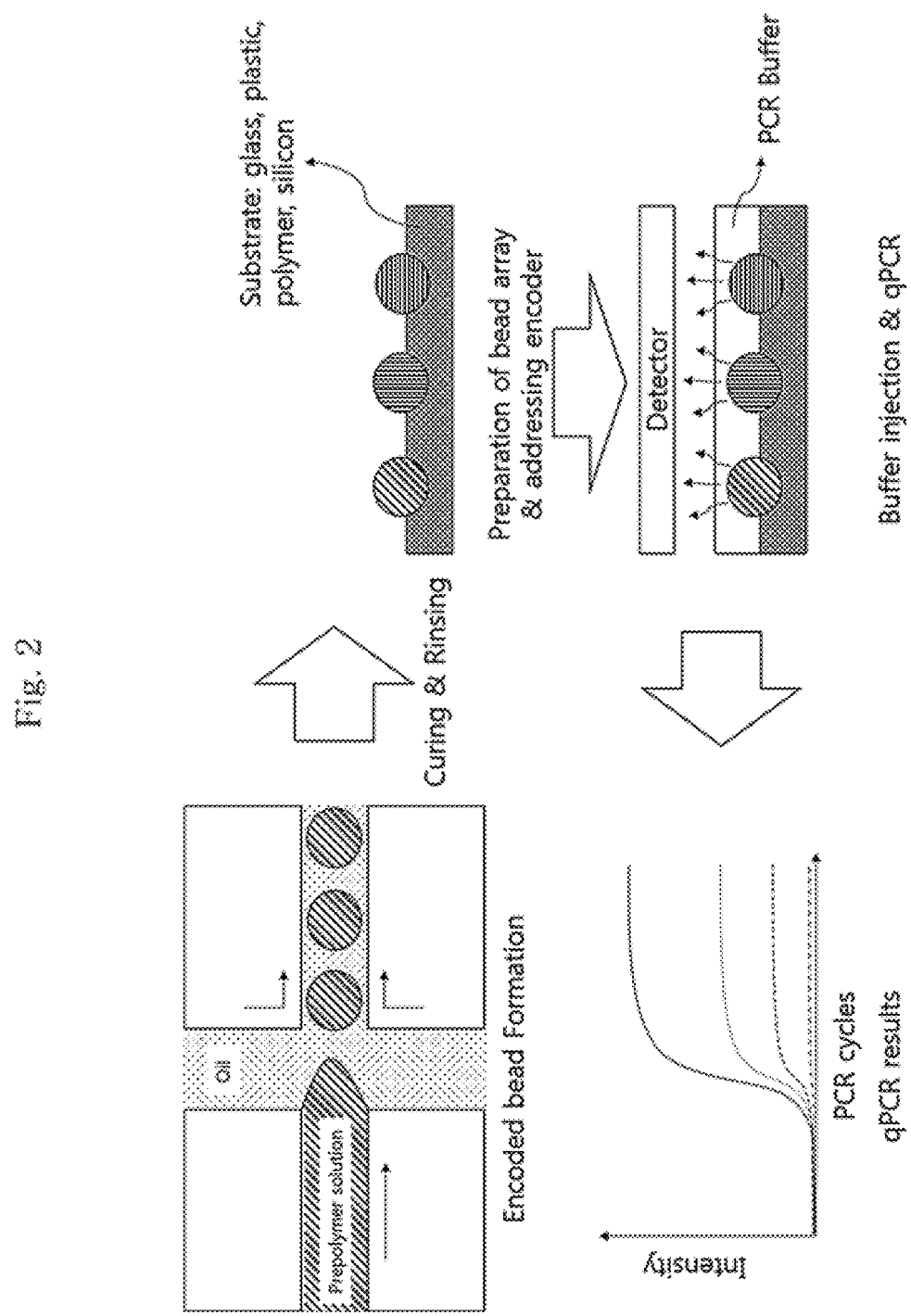
FIG. 2 is a schematic diagram illustrating a method for manufacturing a porous structure according to an embodiment of the present invention (upper left), the arrangement of the porous structures that are manufactured by the above method and have different kinds of targets from one another on an array (upper right), the detection of a nucleic acid in real time while amplifying it (lower right), and the analysis of it (lower left).

Another embodiment of the present invention is a method for manufacturing the porous structure as described above and provides a method (see FIG. 2) for manufacturing a porous structure which includes:

preparing a structure-forming solution containing a pre-polymer, a porogen, and primers in one or more directions between a forward primer and a reverse primer of a target nucleic acid as a primer of polymerase chain reaction (PCR);

forming a structure in a droplet form by allowing oil to pass through one channel of micro-channels consisting of two channels including a section to cross each other at right angles and allowing the structure-forming solution prepared above to pass through the other channel so as to disperse the structure-forming solution in an oil phase in the crossing section;

curing the structure thus formed; and forming pores in the structure by removing the porogen from the cured structure.

As an embodiment, in the step of forming a structure in a droplet form, it is possible to effectively disperse the structure-forming solution in the oil phase in the crossing section by allowing the oil to continuously pass through one channel and the structure-forming solution thus prepared to discontinuously pass through the other channel. At this time, the flow rate of the oil is specifically from 50 to 1500 μl/hr or from 100 to 1200 μl/hr and more specifically from 200 to 400 μl/hr, and the flow rate of the structure-forming solution is specifically from 5 to 1000 μl/hr or from 10 to 500 μl/hr, and more specifically it can be adjusted to from 50 to 150 μl/hr. The particle size of the droplet passing through the channel can be adjusted by adjusting the respective flow rates of the oil and the structure-forming solution and the ratio thereof, whereby it is possible to adjust the particle size of the porous structure to be manufactured. For example, it is possible to prepare a droplet having a particle size of from 10 to 500 μm and more specifically from 42 to 200 μm in a case in which the oil and the structure-forming solution pass through the channels in the respective flow rate ranges. In addition, it is possible to easily manufacture porous structures having various particle sizes by adjusting the respective flow rates as described above, and thus it is possible to distinguish or identify the primers included in the porous structures by using the difference of the particle size without using an encoder.

At this time, the oil adds the shear force to the flow of the porous structure-forming solution of a disperse phase so as to be formed into a droplet form and stabilizes the droplet so as not to be aggregated again. The channel according to an embodiment through which the structure-forming solution passes may have a shape of which the passage is narrowed immediately after the crossing section, and the solution is effectively formed into a droplet as it passes through the channel in this case (see FIG. 6 (B)).

As an embodiment, fluorocarbon (FC) oil, mineral oil, silicone oil, hexadecane, hexane, toluene, benzene, N,N-dimethylformamide (DMF), dichloromethane (DCM), diethyl ether, and the like may be used as the oil.

In addition, still another embodiment of the present invention is a method for manufacturing a porous structure and provides a method (see FIG. 3) for manufacturing a porous structure which includes:

preparing a structure-forming solution containing a pre-polymer, a porogen, and primers in one or more directions between a forward primer and a reverse primer of a target nucleic acid as a primer of polymerase chain reaction (PCR);

forming a structure in a droplet form by spotting the structure-forming solution prepared above on an array;

curing the structure; and forming pores in the structure by removing the porogen from the cured structure.

More specifically, as the array, an array having a surface patterned in a well form may be used so that the porous structures are arranged. According to an embodiment, it is possible to manufacture the porous structures by spotting the porous structure-forming solution at constant locations on the array, and thus it is possible to distinguish different primers included in the respective porous structures from one another by the locations on the array without separately using an encoder.

At this time, the "pre-polymer" means a pre-polymer of which the polymerization or polycondensation reaction is stopped at an appropriate stage in order to facilitate the molding of the polymer, and it means a polymer in a state of not being cured so as to be easily molded in the case of the present invention.

The structure-forming solution according to an embodiment includes a primer only in one direction between the forward primer and the reverse primer of the target nucleic acid as the primer of polymerase chain reaction (PCR), and in this case, the other kind of primer may be separately introduced into the apparatus for multiplex real-time nucleic acid amplification (multiplex real-time PCR) utilizing the porous structure.

Moreover, it is possible to manufacture a plurality of porous structures including different primers from one another by injecting different kinds of primers depending on the kind of the target nucleic acid by using the manufacturing method of the present invention. In addition, the structure-forming solution may further include one or more between an encoder to provide the information of the fixed primer and a fluorescent marker to provide the quantitative information of the nucleic acid to be amplified.

As an embodiment, the step of preparing a structure-forming solution further includes adjusting the size of the pores to be formed in the porous structure by changing the size of the porogen contained in the solution. At this time, as the porogen, for example, polyethylene glycol (PEG) may be used, and specifically, PEG200, PEG300, PEG400, PEG600, PEG1000, PEG1500, PEG2000, PEG3000, PEG3350, PEG4000, PEG6000, PEG8000, PEG10000, PEG12000, PEG20000, PEG35000, PEG40000, and the like (manufacturer: Sigma Aldrich) may be used.

The micro-channel can be manufactured by patterning a substrate into a channel shape on a wafer by photolithography and then casting a mold of this. At this time, as the material for the micro-channel manufactured by casting a mold, any material may be used without limitation as long as it is a silicone-based polymer, and for example, polydimethylsiloxane (PDMS) may be used.

Furthermore, as an embodiment of the present invention, the curing of the porous structure is that the porous structure is cured while maintaining the shape thereof before being cured, and the curing method is not limited as long as the shape can be maintained, and an optical, chemical, or thermal curing method may be used.

Another embodiment of the present invention provides an apparatus for multiplex real-time nucleic acid amplification which includes:

one or more porous structures described above; and an array having a surface patterned in a well form so that the porous structure is arranged.

The material for the array having a surface patterned in a well form according to an embodiment may be glass, a plastic, a polymer, silicone, or the like, and the kind thereof is not limited. As an embodiment, the apparatus for multiplex real-time nucleic acid amplification may include a plurality of porous structures including a primer or a primer and an encoder for each of different target nucleic acids in each of the wells in order to detect various kinds of target nucleic acids at the same time.

In addition, another embodiment of the present invention is a multiplex real-time nucleic acid amplifying method and provides a multiplex real-time nucleic acid amplifying method which includes:

injecting one or more porous structures according to claim 1 into a chamber including an array having a surface patterned in a well form and arranging the porous structures on the array;

injecting a solution containing one or more target nucleic acids into the chamber in an apparatus for multiplex real-time nucleic acid amplification and introducing the solution into a pore of the porous structure; and amplifying the target nucleic acid through the polymerase chain reaction (PCR) of the target nucleic acid.

The porous structure according to an embodiment of the present invention includes a primer only in one direction between the forward primer and the reverse primer of the target nucleic acid as the primer of polymerase chain reaction (PCR), and the solution containing a target nucleic acid includes the other kind of primer. The solution containing a target nucleic acid further includes a primer containing a locked nucleic acid (LNA) such as a 3'-locked nucleic acid primer, a Taq polymerase, and the like as an embodiment.

Moreover, the present invention further includes a step of quantitatively analyzing the nucleic acid that is polymerized in each of one or more porous structures at the same time as the step of conducting the polymerase chain reaction in real time as an embodiment, and thus it is possible to detect and quantitatively analyze different kinds of target nucleic acids in real time while simultaneously amplifying them as described above.

EMBODIMENTS

Hereinafter, the present invention will be described in detail with reference to Experimental Examples of the present invention. These are only illustratively suggested in order to describe the present invention in more detail, but it will be apparent to those having the ordinary skill in the art that the scope of the present invention is not limited by these Experimental Examples.

Example 1

Manufacture 1 of Porous Structure

The method for manufacturing a porous structure according to an embodiment of the present invention will be described below.

Manufacture of Micro-Channel

First, channels were patterned on the silicon wafer SU-8 (product name: 2050, manufacturer: MicroChem) into a shape so as to have a section at which two channels cross each other at right angles using photolithography, thereby manufacturing a mold. Subsequently, a pre-polymer solution prepared by mixing a polydimethylsiloxane (PDMS) solution with a curing agent (product name: SYLGARD® 184, manufacturer: DOW HITECH SILICON) at 10:1 was poured into the mold manufactured using the SU-8. The gas was removed from the pre-polymer in a vacuum chamber for 60 minutes, and the pre-polymer was cured for 90 minutes in an oven at 80° C. and separated from the mold, thereby manufacturing a PDMS micro-channel. At this time, the width of the channel was 120 μm, and the height thereof was 100 μm.

Preparation of Porous Structure-Forming Solution

First, 100 ml of 3×TET solution (3×TE buffer with Tween 20) was prepared by mixing 94.5 mL of distilled water, 3 mL of 100×TE buffer, and 2.5 mL of 10% Tween 20 diluted solution. Thereafter, total 1 mL of a hydrogel solution was prepared by mixing 400 μl of polyethylene glycol 600 (PEG 600) and 200 μl of PEG700DA (manufacturer: Sigma Aldrich) as a porogen, and 50 μl of the Darocur (manufacturer: Sigma Aldrich) and 350 μl of TET as a photoinitiator. Subsequently, 6 μl of a 1 mM primer to bond with the target nucleic acid was mixed with 54 μl of the TE buffer so as to have 100 M (60 μl) in total, and this was mixed with the hydrogel solution (540 μl), thereby preparing a hydrogel pre-polymer solution having a final primer concentration of 10 μM (600 μl).

At this time, the kind of the target nucleic acid was *salmonella* food poisoning bacteria (microbiological resource center KCTC #2515), and a porous structure-forming solution including the following forward primer as a primer, a porous structure-forming solution including the following reverse primer as a primer, and a porous structure-forming solution including both of these as a primer were prepared, respectively. At this time, the fluorescent marker was the SYBR® Green I (manufacturer: Invitrogen).

Forward primer: AAT TAT CGC CAC GTT CGG GCA ATT CGT TA (SEQ ID NO. 1),
Reverse primer: TCA ATA ATA CCG GCC TTC AAA TCG GCA TC (SEQ ID NO. 2)

Manufacture of Porous Structure

A structure in a droplet form was manufactured by a flow-focusing method in which fluorocarbon (FC) oil containing the 1.8% Krytox® surfactant (Manufacturer: Dupont) was continuously injected into one channel between the two crossing micro-channels thus manufactured and the hydrogel pre-polymer solution thus prepared was discontinuously injected into the other channel so as to be dispersed in the oil in the crossing section.

At this time, the flow rates of the FC oil (continuous phase) and the hydrogel pre-polymer solution (disperse phase) were adjusted as presented in Table 1 so that the respective structures had various particle sizes of from 71 to 131 μm.

TABLE 1

| Flow rate of FC oil (μl/hr) | Flow rate of hydrogel pre-polymer solution (μl/hr) | Size of droplet (μm) |
|---|---|---|
| 200 | 100 | 129 |
| 300 | 100 | 120 |
| 400 | 100 | 106 |
| 500 | 100 | 81 |
| 300 | 200 | 131 |
| 500 | 200 | 113 |
| 600 | 200 | 88 |
| 1200 | 400 | 71 |

Figure 4A:
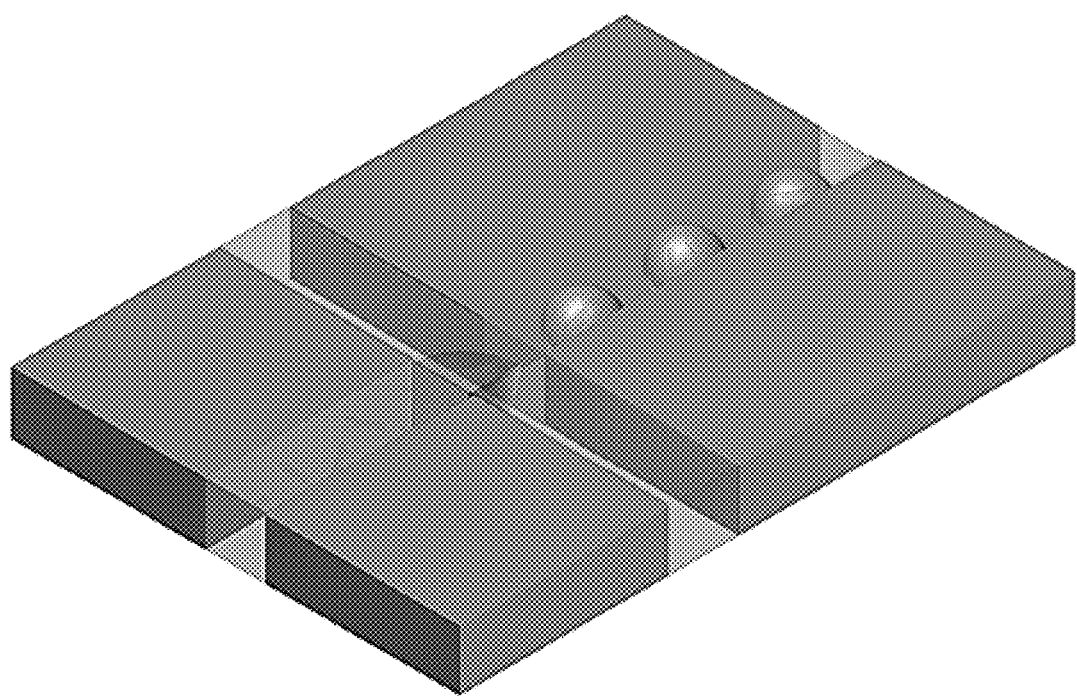
FIG. 4 (A) is a schematic diagram illustrating a process of manufacturing a structure in a droplet form by using a micro-channel in accordance with the method according to an embodiment of the present invention, and FIG. 4 (B) is an actually taken photograph of the process.
Figure 4B:
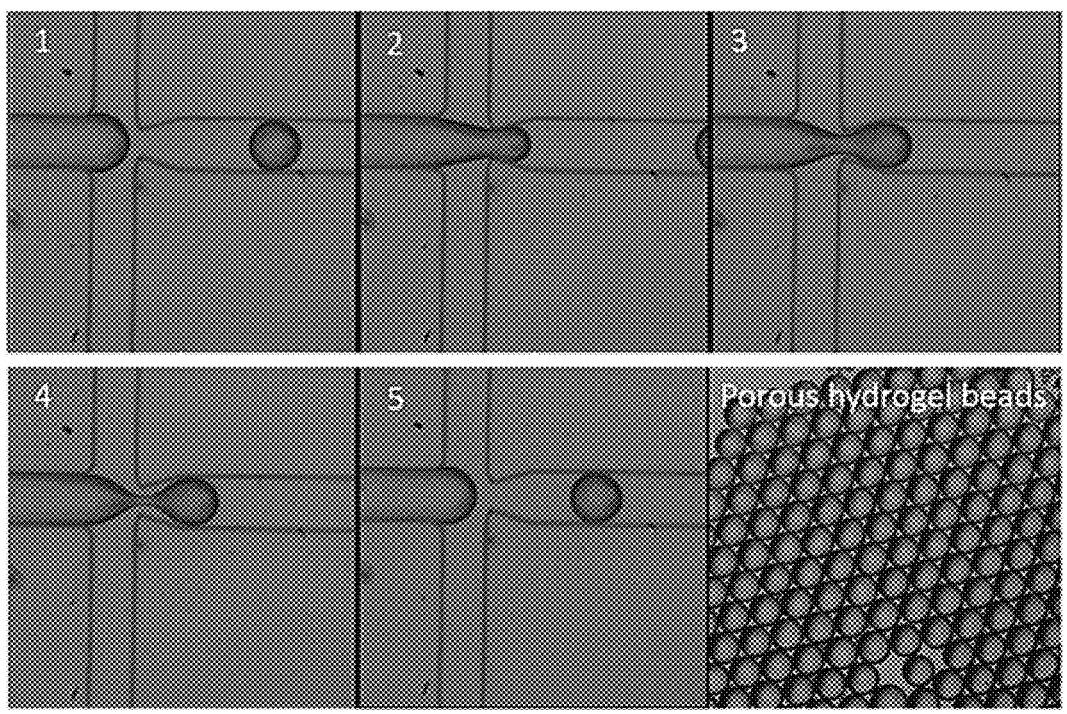
Figure 5:
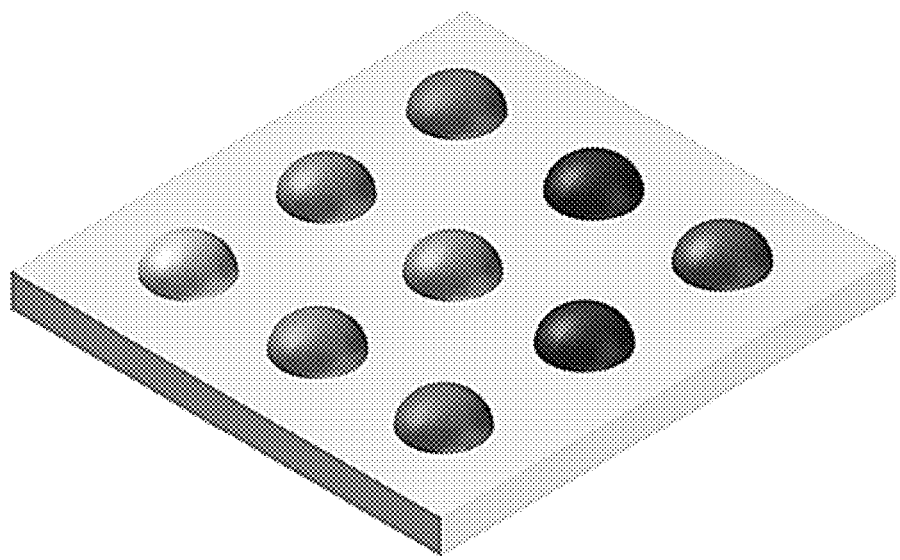
FIG. 5 is a schematic diagram illustrating a method for manufacturing a structure in a droplet form by spotting a structure-forming solution on an array in accordance with the method according to an embodiment of the present invention, and at this time, various shades of the structures indicate that different kinds of primers are included in the respective structures.

FIG. 4 (A) is a schematic diagram illustrating the process of forming a structure in a droplet form by using a micro-channel in accordance with the method described above, and FIG. 4 (B) is an actually taken photograph of the manufacturing process in which the flow rate of FC oil is 300 μl/hr and the flow rate of the hydrogel pre-polymer solution is 100 μl/hr.

Thereafter, the structure in a droplet form thus manufactured was irradiated with ultraviolet light (UV) at from 6 to 8 mW/cm² for 20 minutes so as to be cured. The structure was rinsed with 200 μl of pure FC oil two times and 200 μl of the TE buffer with Tween 20 five times to remove the porogen, thereby manufacturing a porous structure having pores formed in the structure at a porosity of 60%.

Example 2

Manufacture 2 of Porous Structure

Next, the manufacture of a porous structure according to another embodiment of the present invention will be described.

The hydrogel pre-polymer solution of a porous structure-forming solution was prepared by the same method as in Example 1 described above. Thereafter, the hydrogel pre-polymer solutions including different primers (forward primer, reverse primer, and forward and reverse primers) from one another were spotted on each well of the array having a surface patterned in a well form so that the porous structure was arranged, thereby forming a structure in a droplet form.

Thereafter, the structure in a droplet form thus manufactured was irradiated with ultraviolet light (UV) at 190.6 mW/cm² for 5 seconds so as to be cured. The structure was rinsed 200 μl of the TE buffer with Tween five times to remove the porogen, thereby manufacturing a porous structure having pores formed in the structure and a particle size of 120 μm.

Example 3

Multiplex Real-Time Nucleic Acid Amplification Using Porous Structure

A method for amplifying a target nucleic acid in real time using the porous structure according to an embodiment of the present invention will be described below.

Figure 6:
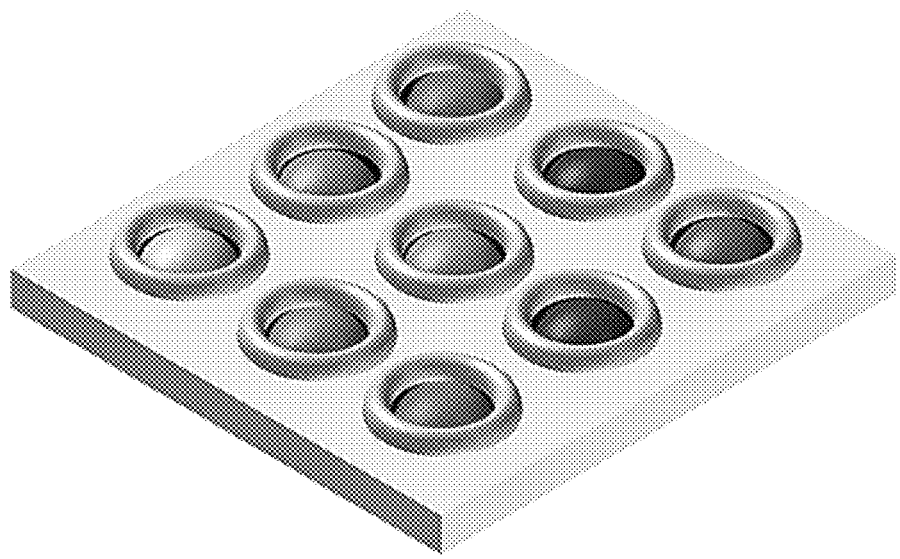
FIG. 6 illustrates a chamber that is used in an embodiment of the present invention and includes an array having a surface patterned in a well form so that the porous structure is arranged.

First, a chamber including an array having a surface patterned in a well form so that the porous structure was arranged was prepared (FIG. 6). Thereafter, the porous structures which were manufactured by the method of Example 1 or 2 described above and included different primers (forward primer, reverse primer, and forward and reverse primers) from one another were injected into the chamber so as to be safely disposed in each well. At this time, the structures which were not safely disposed in each well but remain around the wells were rinsed off. Subsequently, 8 µl of the PCR Mastermix (containing a polymerase and a nucleotide, manufacturer: Nano-Bio System Lab.), 5.4 µl of distilled water (D.I. Water), and 1 µl of *salmonella* DNA template ($1\times10^6$ copies of plasmid DNA) were introduced into the chamber, and a PCR solution including the other primer was injected into the chamber in a case in which the porous structure included only one between the forward primer and the reverse primer.

Thereafter, the total polymerase chain reaction (PCR) was allowed to proceed in accordance with the following temperature cycle, thereby amplifying the nucleic acid. At this time, the PCR reaction was conducted 40 cycles in total, and the quantitative analysis was conducted by measuring the fluorescence intensity exhibited by the fluorescent marker in the amplified nucleic acid for 5 seconds whenever every cycle is completed.

Figure 7:
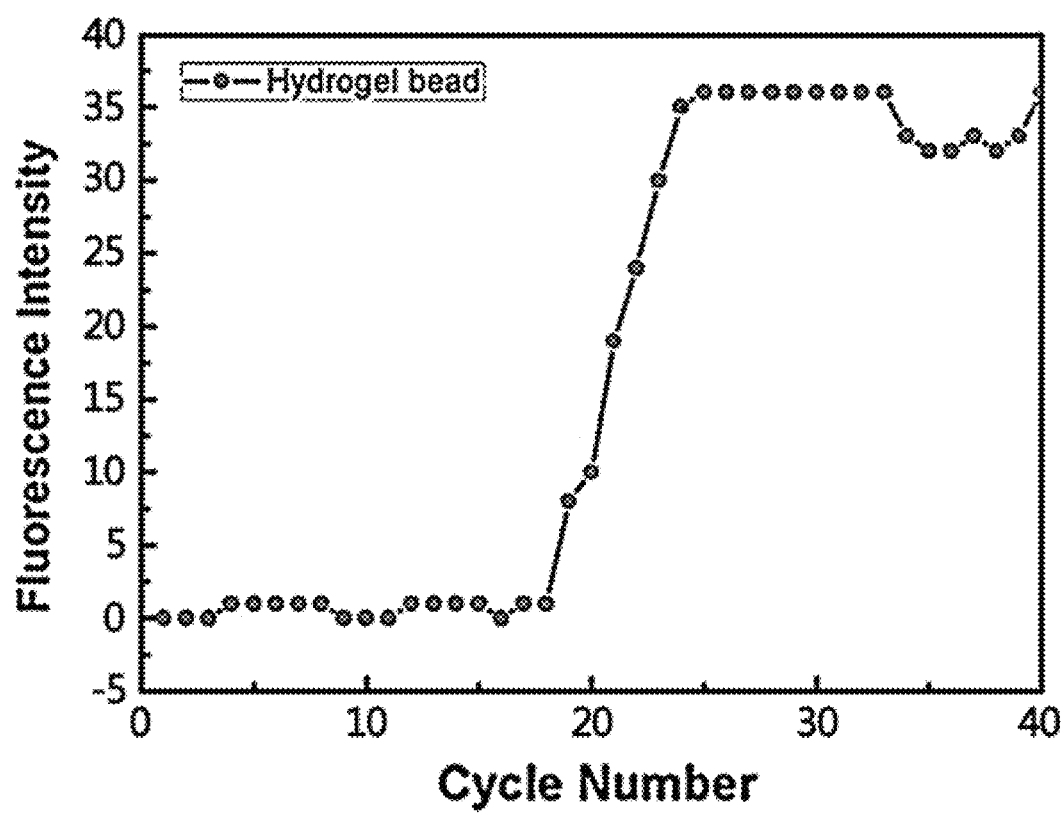
FIG. 7 is a graph illustrating the results for the quantitative PCR of the porous structure manufactured in accordance with the method according to an embodiment of the present invention.

Pre-denaturation: 95° C., 8 seconds,
Denaturation: 95° C., 3 seconds,
Annealing and extension: 72° C., 6 seconds FIG. 7 is a graph illustrating the results for the quantitative PCR (qPCR) of the porous structure which is manufactured by the same method as the manufacturing method of Example 1 by fixing only the forward primer between the forward primer and the reverse primer and has a particle size of 120 µm, and as illustrated in the graph, it can be seen that the PCR normally takes place.

Experimental Example 1

Comparison of Efficiency of Quantitative PCR Depending on Kind of Primer to be Fixed to Porous Structure The following experiment was conducted in order to compare the efficiency of the quantitative PCR depending on the kind of the primer to be fixed to the porous structure.

The porous structures were manufactured in the same manner except that the porous structure Ch1-3 was manufactured by the method of Example 2, only the forward primer was fixed to the porous structure Ch1, and both the forward primer and the reverse primer were fixed to the porous structure Ch2. Only the PCR solution was included in Ch3 without including the porous structure of the present invention, and Ch3 was used as a control. At this time, the amount of the primer included in a porous structure was 100 µM, and the particle size of the porous structure was 600 µm.

Thereafter, the polymerase chain reaction (PCR) was conducted 40 cycles in total by the method of Example 3 described above, and the photographs of the porous structure taken before and after the qPCR using a CCD (charge-coupled device) camera is illustrated in FIG. 8. In addition, the photograph (left) of the porous structure Ch1-3 subjected to electrophoresis in order of from channel 1 to channel 3 and then measurement and the graph of fluorescence intensity measured for every cycle are illustrated in FIG. 9.

From the experimental results, it can be seen that the nucleic acid amplification factor of the porous structure Ch1 to which only the forward primer is fixed is superior as the fluorescence intensity thereof is significantly higher than that of the porous structure Ch2 to which both of the primers are fixed as illustrated in FIG. 8 and FIG. 9. This means that the degree of freedom of the primer is higher and thus the reactivity is higher in a case in which one primer is fixed than in a case in which two primers are fixed.

In addition, in the results for electrophoresis illustrated on the left of FIG. 9, it can be seen that there is no band for Ch1 and Ch2 but there is a band for Ch3. This is because the primer is fixed to the porous structure in Ch1 and Ch2 and thus a band does not appear when loading on the gel.

Experimental Example 2

Comparison of Efficiency of Quantitative PCR Depending on Condition (Presence or Absence of Linker) of Primer to be Fixed to Porous Structure The flowing experiment was conducted in order to compare the efficiency of the quantitative PCR depending on the conditions of the primer to be fixed to the porous structure.

The porous structure Ch1 to which the forward primer and the reverse primer were fixed and the porous structure Ch2 to which the forward and the reverse prime linked via a linker were fixed were manufactured in the same manner by the same method as the manufacturing method of Example 2 described above except that the porogen was removed by rinsing with the TET buffer of 161 µl five times. At this time, the amount of the primer included in the porous structure was 100 µM and the particle size of the porous structure was 600 µm. Only the PCR solution was included in Ch3 without including the porous structure of the present invention, and Ch3 was used as a control.

The linker fixed to the forward primer and reverse primer of Ch2 described above is polyethylene glycol (PEG, n=50), and the forward primer and reverse primer to which this linker is fixed are as follows.

Forward primer linked to linker (long forward primer): 5'-Acrydite-PEG (polyethylene glycol, n=50)-DNA (AAT TAT CGC CAC GTT CGG GCA ATT CGT TA)-3' (SEQ ID NO. 1), Reverse primer linked to linker (long reverse primer): 5'-Acrydite-PEG (polyethylene glycol, n=50)-DNA (TCA ATA ATA CCG GCC TTC AAA TCG GCA TC)-3' (SEQ ID NO. 2)

Figure 10A:
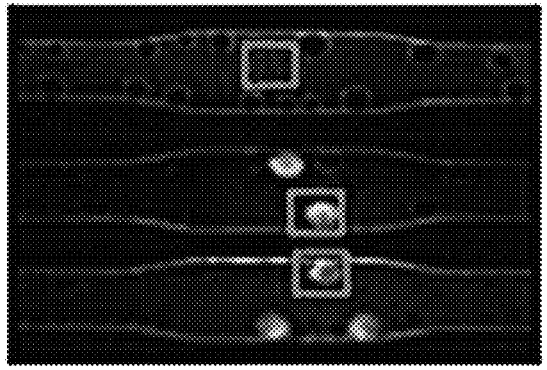
FIG. 10 illustrates photographs of the porous structure Ch1-3 according to an embodiment of the present invention taken (a) before qPCR, (b) during qPCR (42th cycle), and (c) after qPCR using a CCD camera.
Figure 10B:
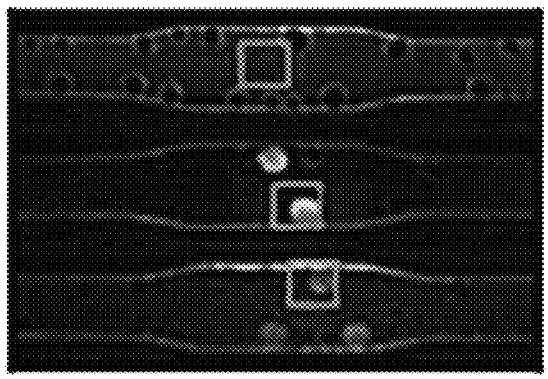
Figure 10C:
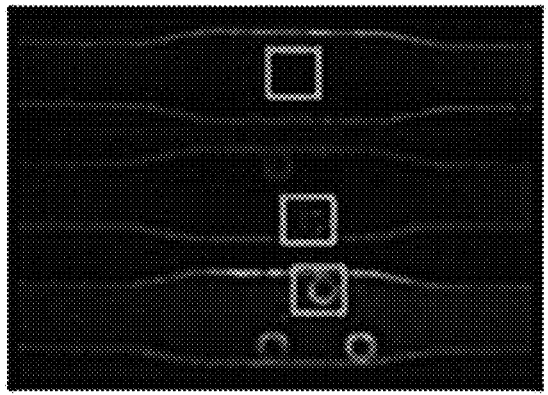

Thereafter, the polymerase chain reaction (qPCR) was conducted by the same method as in Example 3 described above except that the qPCR was conducted 90 cycles in total. The photographs of the porous structure taken (a) before qPCR, (b) during qPCR (42th cycle), and (c) after qPCR using a CCD camera are illustrated in FIG. 10. It is confirmed that the qPCR proceeds since the fluorescent image appears as the cycle increases. In addition, the graph of the fluorescence intensity measured for every cycle is illustrated in FIG. 11.

From the results illustrated in FIG. 11, it can be seen that the fluorescence intensity is higher in the case of Ch2 in which the primer is linked to the porous structure via a linker than in the case of Ch1 as a result of qPCR, and this is because the degree of freedom of the primer in the porous structure Ch2 is higher than in Ch1 in which the primer is not linked to the porous structure via a linker.

INDUSTRIAL APPLICABILITY

The porous structure according to the present invention is used in multiplex real-time nucleic acid amplification (multiplex real-time PCR) since it is possible to simultaneously detect various kinds of target nucleic acids and at the same time to analyze these in real time, and the porous structure is useful for the fields that require an accurate diagnosis of diseases through simultaneous and rapid analysis of many different kinds of nucleic acids such as point-of-care technology (POCT).

The invention claimed is:

1. A porous structure comprising a cured polymer having pores,
the porous structure comprising primers in one or more directions between a forward primer and a reverse primer of a target nucleic acid as a primer of polymerase chain reaction (PCR) fixed to the interior of the pores,
wherein a porosity of the porous structure is from 60 vol % to 80 vol % with respect to a total volume of the porous structure.

2. The porous structure according to claim 1, wherein a primer only in one direction between a forward primer and a reverse primer of a target nucleic acid is fixed to the porous structure as a primer of polymerase chain reaction (PCR).

3. The porous structure according to claim 1, wherein the porous structure is from 10 μm to 500 μm in size.

4. The porous structure according to claim 1, wherein a primer fixed to the interior of a pore of the porous structure includes an acryl group at a terminal, wherein the acryl group is chemically fixed to the porous structure.

5. The porous structure according to claim 1, wherein one or more primers among the primers fixed to the interior of a pore of the porous structure are linked to the porous structure via a linker.

6. The porous structure according to claim 5, wherein a length of the linker is from 5 nm to 100 nm.

7. The porous structure according to claim 1, further comprising an encoder to provide information corresponding to a fixed primer.

8. An apparatus for multiplex real-time nucleic acid amplification comprising:
one or more porous structures according to claim 1; and
an array having a surface patterned in a well form so that the porous structure is arranged.

9. The apparatus for multiplex real-time nucleic acid amplification according to claim 8, comprising a plurality of porous structures including a primer for each of different target nucleic acids.

10. The apparatus for multiplex real-time nucleic acid amplification according to claim 8, wherein a plurality of the one or more porous structures have different sizes depending on the kind of primers included therein.

11. The porous structure according to claim 1, further comprising a fluorescent marker to provide quantitative information corresponding to a nucleic acid to be amplified in a pore.

12. The porous structure according to claim 1, wherein the size of the porous structure is configured to identify the primer of PCR fixed to the interior of the pores.

13. The porous structure according to claim 1, wherein the primer is fixed to the interior of the pores in a concentration of from 10 μM to 100 μM.

* * * * *